(12) United States Patent
Nichols

(10) Patent No.: US 9,750,551 B1
(45) Date of Patent: Sep. 5, 2017

(54) BUNION REPAIR METHOD AND TOOL ASSEMBLY

(71) Applicant: Donald Nichols, Wheaton, IL (US)

(72) Inventor: Donald Nichols, Wheaton, IL (US)

(73) Assignee: Donald Nichols, Wheaton, IL (US)

( * ) Notice: Subject to any disclaimer, the term of this patent is extended or adjusted under 35 U.S.C. 154(b) by 311 days.

(21) Appl. No.: 14/632,901

(22) Filed: Feb. 26, 2015

Related U.S. Application Data

(60) Provisional application No. 61/945,016, filed on Feb. 26, 2014.

(51) Int. Cl.
| | |
|---|---|
| *A61B 17/88* | (2006.01) |
| *A61B 17/80* | (2006.01) |
| *A61B 17/68* | (2006.01) |
| *A61B 17/16* | (2006.01) |
| *A61B 17/56* | (2006.01) |

(52) U.S. Cl.
CPC ...... *A61B 17/8061* (2013.01); *A61B 17/1682* (2013.01); *A61B 17/683* (2013.01); *A61B 17/8004* (2013.01); *A61B 2017/564* (2013.01)

(58) Field of Classification Search
None
See application file for complete search history.

(56) References Cited

U.S. PATENT DOCUMENTS

| | | | | |
|---|---|---|---|---|
| 5,637,112 A | * | 6/1997 | Moore | ............ A61B 17/0469 606/139 |
| 7,875,058 B2 | | 1/2011 | Holmes, Jr. | |

\* cited by examiner

*Primary Examiner* — Sameh Boles
(74) *Attorney, Agent, or Firm* — Erickson Law Group, PC

(57) ABSTRACT

A system and method for the surgical correction of a bunion deformity allows for correction of a bunion deformity. The method includes: drilling a hole across a first metatarsal and through a second metatarsal; placing a tube from outside the first metatarsal through the hole across the first and second metatarsals; pushing a first button through the tube until the first button exits the tube through a medial side of the second metatarsal; flipping the first button to engage the first button against the second metatarsal and applying a lateral tension on the suture strand; manually pushing the first metatarsal and the second metatarsal together to correct intermetatarsal angular deformity; pulling free ends of the suture strand of the suture-button construct to advance a second button of the suture-button construct and to engage the second button against the first metatarsal; and securing the second button against the first metatarsal.

7 Claims, 10 Drawing Sheets

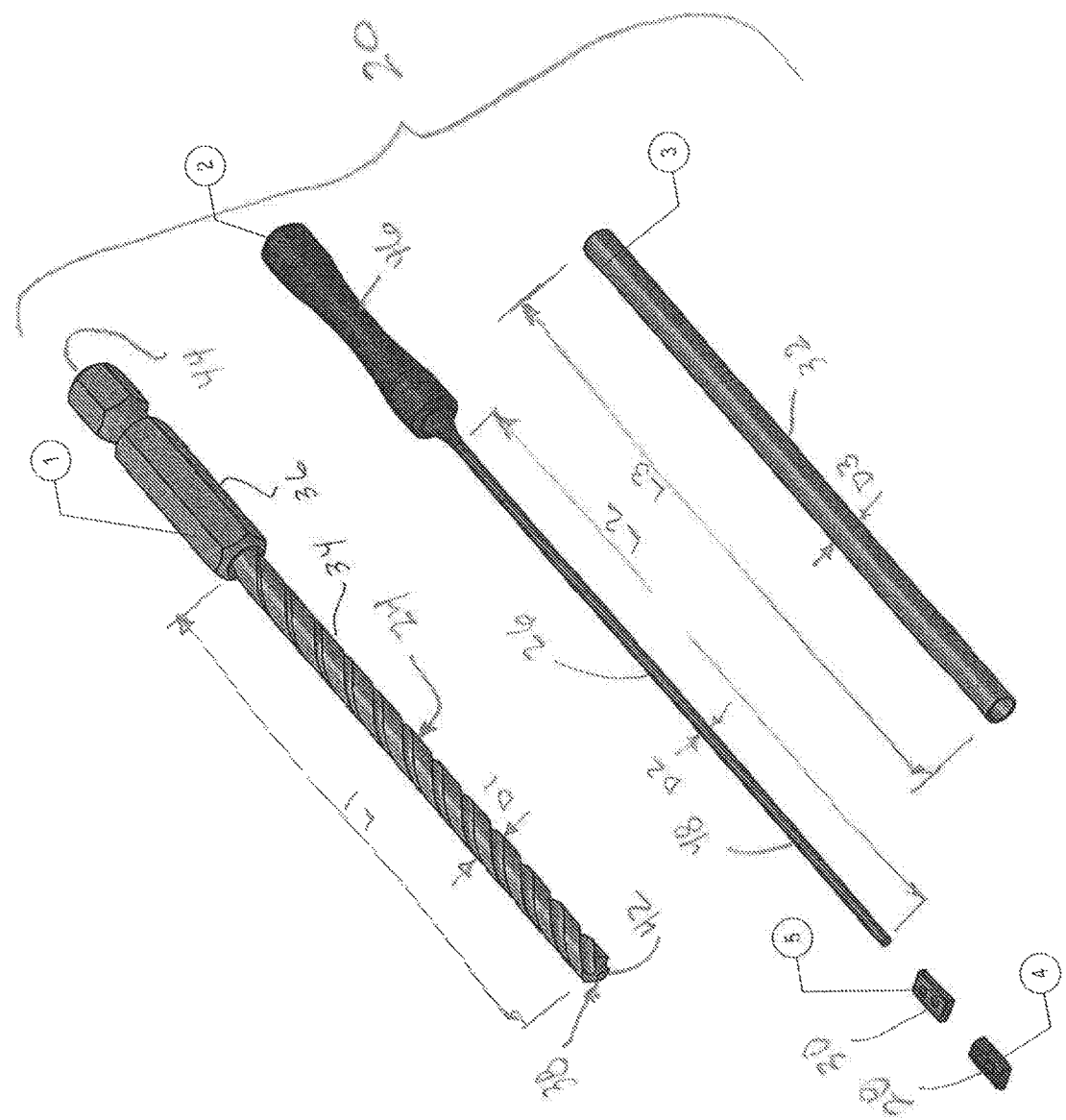

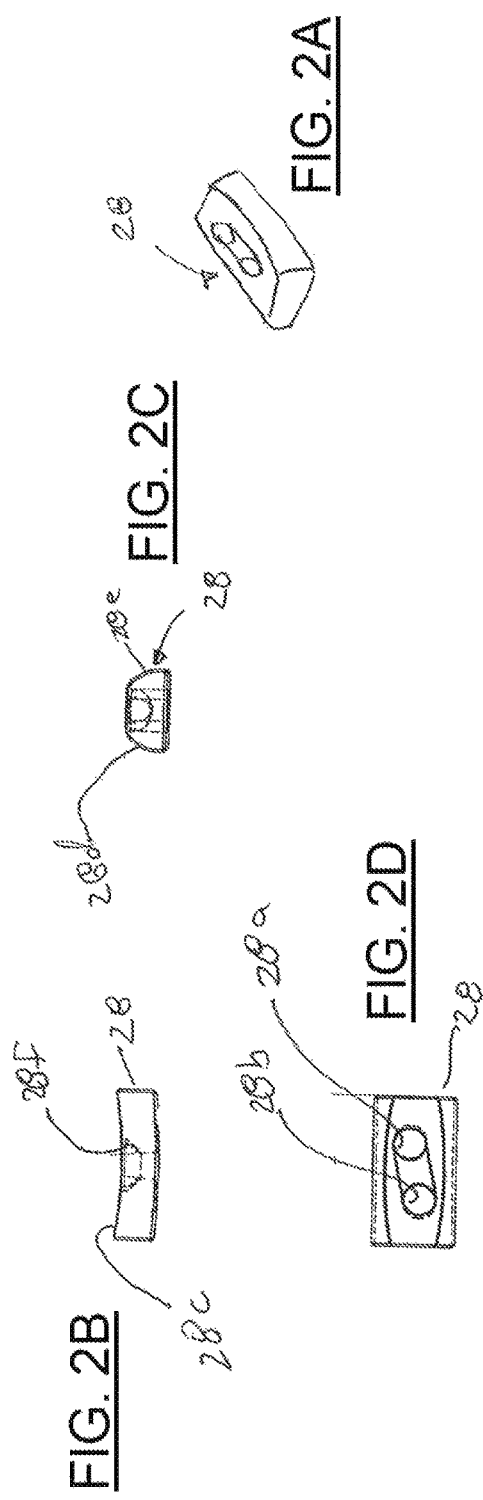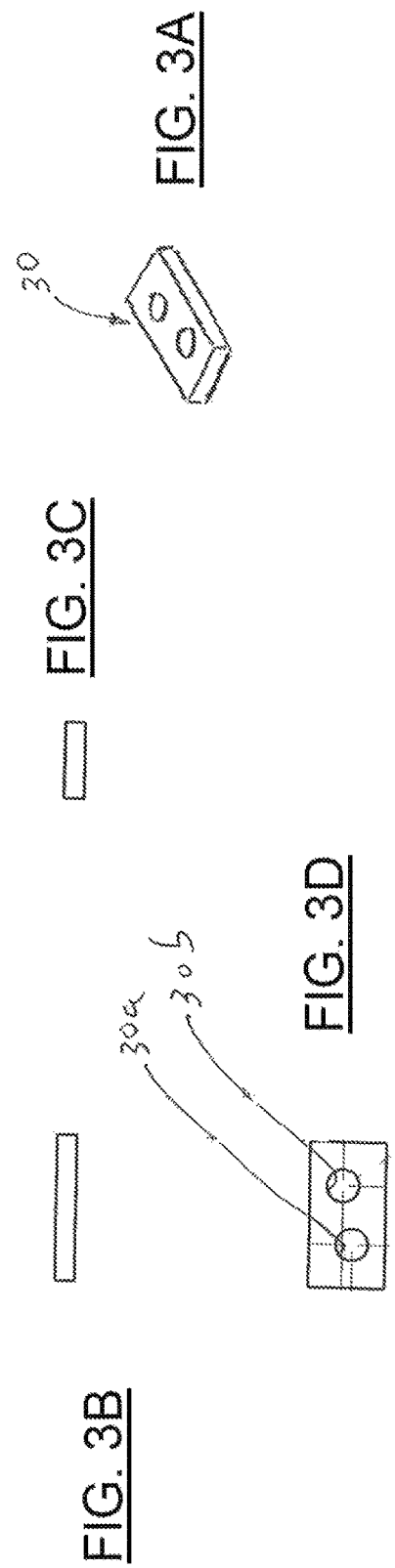

BUNION REPAIR METHOD AND TOOL ASSEMBLY

This Application claims the benefit of U.S. Provisional Application 61/945,016 filed Feb. 26, 2014.

BACKGROUND

The present invention relates to the field of surgery and, in particular, to a bunion repair method.

Bunions can be associated with a deviation in the angle between the first and second metatarsal bones of the foot.

A bunion repair is a surgical procedure performed on the first toe joint. The purpose is to correct a deformity of the toe or to remove a painful bunion at its base. Surgical procedures may include removing the abnormal bony enlargement of the first metatarsal, realigning the first metatarsal relative to the adjacent metatarsal, straightening the toe relative to the first metatarsal and adjacent toes, or correcting any abnormal misalignment within the first toe.

U.S. Pat. No. 7,875,058 describes a surgical procedure that involves making an incision into the skin and carefully working down to the great toe joint and bone. The first metatarsal is typically cut with a bone saw and corrections are made. These corrections are kept in place with a first and a second button held together by a suture extending across the first and second metatarsal.

The method described in U.S. Pat. No. 7,875,058 includes inserting a guide wire, and using a cannulated drill bit, drilling a hole across the first metatarsal and through the second metatarsal. A pull-through needle with a pull-through suture strand is passed through the hole to a medial of the first metatarsal and stopped before a first button enters the hole. The pull-through suture strand is pulled such that the first button lies sideways for passage through the hole. The first button of the construct is advanced through the hole until it exits the hole through the first metatarsal on the medial side of the first metatarsal cortex. Upon exiting the hole, the first button is flipped and a lateral tension is applied on the first suture strand to seat the first button against the first metatarsal. The pull-through suture is then cut and removed and the first button is anchored. Subsequently, the free ends of the first suture strand are pulled to advance the second button of the construct to seat the second button against the second metatarsal.

The present inventor has recognized that it would be advantageous to minimize the incisions necessary to undergo the procedure of stabilizing the first metatarsal against the second metatarsal. The present inventor has recognized that it would be advantageous to improve the prior art techniques to reduce the chance of a stress fracture of the first or second metatarsal.

SUMMARY

The present invention provides a system designed for ease and speed for the surgical correction of a bunion deformity. The method is particularly advantageous for a flexible bunion deformity. A flexible bunion is often described by the amount of sagital plane motion of the first metatarsal at the articulation with the medial cuneiform. Unfortunately, the greatest variable in bunion correction is in fact the motion of the first metatarsal at the articulation of the medial cuneiform in the transverse plane, the transverse plane being generally the plane of the paper of FIGS. 4A-4G. The method allows for open or minimally invasive bunion repair, which reduces surgical and thus anesthesia time, both reducing complications (risk of DVT, Pulmonary Atelectasis, infection, complications associated with use of longer tourniquet times, urinary issues, etc). The smaller incisions reduce bleeding and allows for a better aesthetic appearance.

The method of the present invention allows correction of a bunion deformity which would have typically been corrected with osteotomies (bone cuts) and screw fixation, or more commonly with an arthrodesis (joint fusion) at the level of the first MT/Cuneiform joint, which typically involves the use of a plate and 5 screws. The method reduces, or eliminates the need for a second incision at the level of the proximal second interspace, the area between the second and third metatarsals near the bases thereof, such as described in U.S. Pat. No. 7,875,058. The method is easier and thus more predictable and re-creatable.

According to the method the first metatarsal is placed in the correct position in the transverse plane by checking the Tibial Sesamoid Position, wherein the tibial sesamoid position is a relationship of the actual tibial sesamoid to the longitudinal bisection of the middle of the first metatarsal head, with use of fluoroscopy (real time x-ray). A 0.045" guide wire from the medial, distal first metatarsal head, where medial is toward the midline of the bone and distal means further from the base, angled proximal lateral to the base of the second metatarsal, is placed and checked with fluoroscopy.

After correct placement of the guide wire is determined, the surgeon drills over this wire coaxially with a cannulated drill bit. The drill bit is removed and is replaced with a tube, making sure with fluoroscopy that the tube exits lateral to the base of the second metatarsal at the area of the metaphyseal/diaphyseal junction, the junction of the shaft and base, and as to not violate the base of the third metatarsal. The guide wire is removed and the tube then facilitates placing FIBER WIRE placed though the flat or curved plate which is then pushed through the tube out the tube lateral to the base for the second metatarsal. The tube is slowly retracted, checking under fluoroscopy that the plate, with its novel design to pull more against the one side of the bone, causing the plate to turn parallel to the shaft of the metatarsal. Due to the eccentric orientation of the holes, this will cause one side of the plate to move faster than the other side when pulling on the suture and thus rotate the plate. This then turns the plate more parallel to the long axis of the bone. This then prevents the plate from exiting back out of the drilled bore due to its length being longer than the bore diameter.

The surgeon pulls on the FIBER WIRE, checking for tension, and with the first metatarsal pushed laterally, reduces the first intermetatarsal angle, the angle between the first and second metatarsals. The FIBER WIRE is tied with or without an additional plate on the medial side of the first metatarsal head, once the guide tube is removed. This then keeps a constant lateral pull on the first metatarsal holding it in the correct position. Without fixation (and especially fusion), this allows for much quicker return to activities, allows for earlier driving, return to work, no risk of delayed or non-union (bone doesn't heal or fuse together), malposition (bone heals in poor position) of capital fragment/fusion site, etc. With increase activity post-operatively this will reduce other post-operative risks such as DVT (deep venous thrombosis), osteopenia, etc.

The method does not require a second incision based on the technique and assembly of tools. Also, there is further obliquity that allows for less chance of a stress fracture. In other words, because the FIBER WIRE is angled with respect to the metatarsals, the bore is formed into the second metatarsal, not at the relatively slender mid diaphysis but at the thicker portion of the second metatarsal and in an area of less anatomic forces. Also, because of the proximity to the base of the second metatarsal, the outer shape of the bone (Cortex of the metaphyseal/diaphyseal junction) is angled and this is accounted for with the plate design. This system makes the procedure easier and more predictable.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 1 is an exploded view of a tool assembly used to perform a method of the present invention;

FIG. 2A is an enlarged perspective view of a first button or plate shown in FIG. 1;

FIG. 2B is an elevation view of the first button or plate shown in FIG. 1;

FIG. 2C is an end view of the first button or plate shown in FIG. 1;

FIG. 2D is a plan view of the first button or plate shown in FIG. 1;

FIG. 3A is an enlarged perspective view of a second button or plate shown in FIG. 1;

FIG. 3B is an elevation view of the second button or plate shown in FIG. 1;

FIG. 3C is an end view of the second button or plate shown in FIG. 1;

FIG. 3D is a plan view of the second button or plate shown in FIG. 1;

DETAILED DESCRIPTION

Figure 4A:
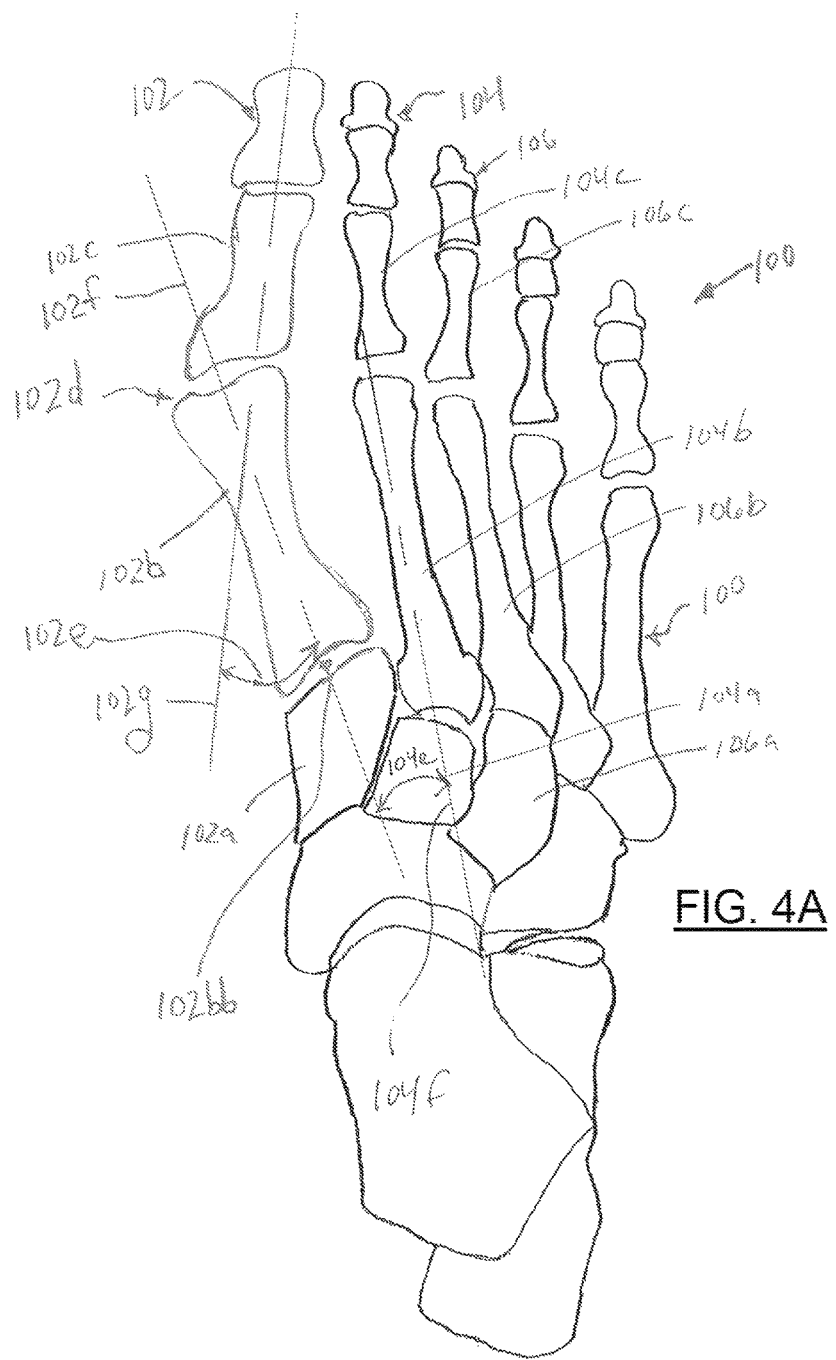
FIG. 4A is a schematic outline of a skeletal foot showing a bunion to be repaired.

While this invention is susceptible of embodiment in many different forms, there are shown in the drawings, and will be described herein in detail, specific embodiments thereof with the understanding that the present disclosure is to be considered as an exemplification of the principles of the invention and is not intended to limit the invention to the specific embodiments illustrated.

U.S. Pat. No. 7,875,058 is herein incorporated by reference to the extent that it does not contradict the disclosure herein.

FIG. 1 illustrates a tool assembly 20 that is used to perform a bunion repair method of the present invention.

The assembly 20 includes a drill bit 24, a pusher 26, a first button or plate 28, a second button or plate 30, and a tube 32.

The drill bit 24 has a drill portion 34 and a base portion 36. The drill portion 34 has a diameter D1 of about 4 mm, and a drill length L1 of about 80 mm.

An axial through bore 38 has a diameter of about 1.2 mm and extends from an open tip end 42 to an open base end 44.

The pusher includes a handle 46, a pushing shank 48 with a diameter D2 of about 1.3 mm and a length L2 of about 100 mm.

The tools shown in FIG. 1 are preferably composed of titanium, although other materials are possible.

FIGS. 2A-2D illustrate the first plate 28. The polate 28 includes two holes 28a, 28b for receiving a suture or FIBER WIRE. The plate 28 has a curved face 28c which allows the plate to fit comformably against the second metatarsal 104b. The plate 28 includes curved sides 28d, 28e. The holes 28a, 28b, are recessed in a groove 28f in the curved face 28c.

FIGS. 3A-3D illustrate the second plate 30. The plate 30 includes two holes 30a, 30b for receiving a suture or FIBER WIRE.

Advantageous dimensions (in mm) for the two plates are shown in FIGS. 2A-3D, although the invention is not limited to any particular dimensions.

The tube 32 has a length L3 of about 90 mm and a diameter D3 of about 3.9 mm with a wall thickness of about 0.25 mm.

FIG. 4A illustrates a skeletal foot 100 having a first toe 102, a second toe 104, and a third toe 106. The bones of the toes include cuneiforms 102a, 104a, 106a; metatarsals 102b, 104b, 106b; and proximal phalanxes 102c, 104c, 106c. FIG. 4A shows that the first metatarsal 102b has been adversely rotated over time outwardly about the interface 102bb between the first metatarsal 102b and the first cuneiform 102a to form an outward projection or bunion 102d. To repair the bunion it is important to straighten the offset angle 102e in the transverse plane between the metatarsal axis 102f and the phalanx axis 102g, and reduce the angle 104e in the transverse plane between the first metatarsal axis 102f and the second metatarsal axis 104f.

Figure 4B:
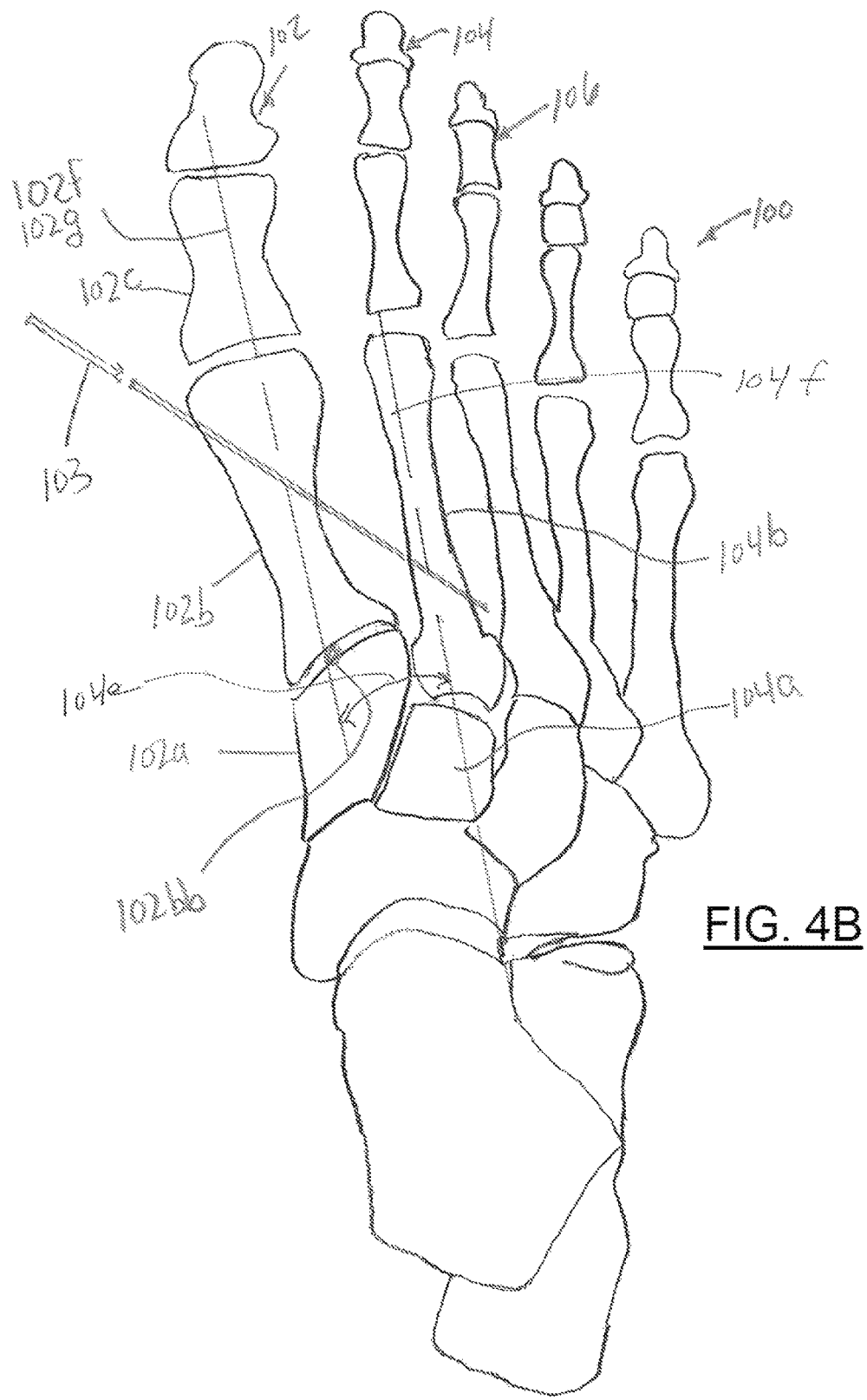
FIG. 4B is a schematic outline of the skeletal foot of FIG. 4A during a first step of bunion repair.

As shown in FIG. 4B the first metatarsal 102b has been rotated clockwise about the interface 102bb, and the metatarsal axis 102f has been substantially aligned with the phalanx axis 102g and the offset angle 102e has been reduced to near zero. A surgical method described in FIGS. 4B-4G will hold the bones in the desired position as shown in FIG. 4B.

In a first step, a K-wire 103 is inserted by a driver through the first metatarsal 102b, spans between the first metatarsal 102b and the second metatarsal 104b and is inserted through the second metatarsal bone 104b. The K-wire 103 can have a diameter of about 0.045 inches.

Figure 4C:
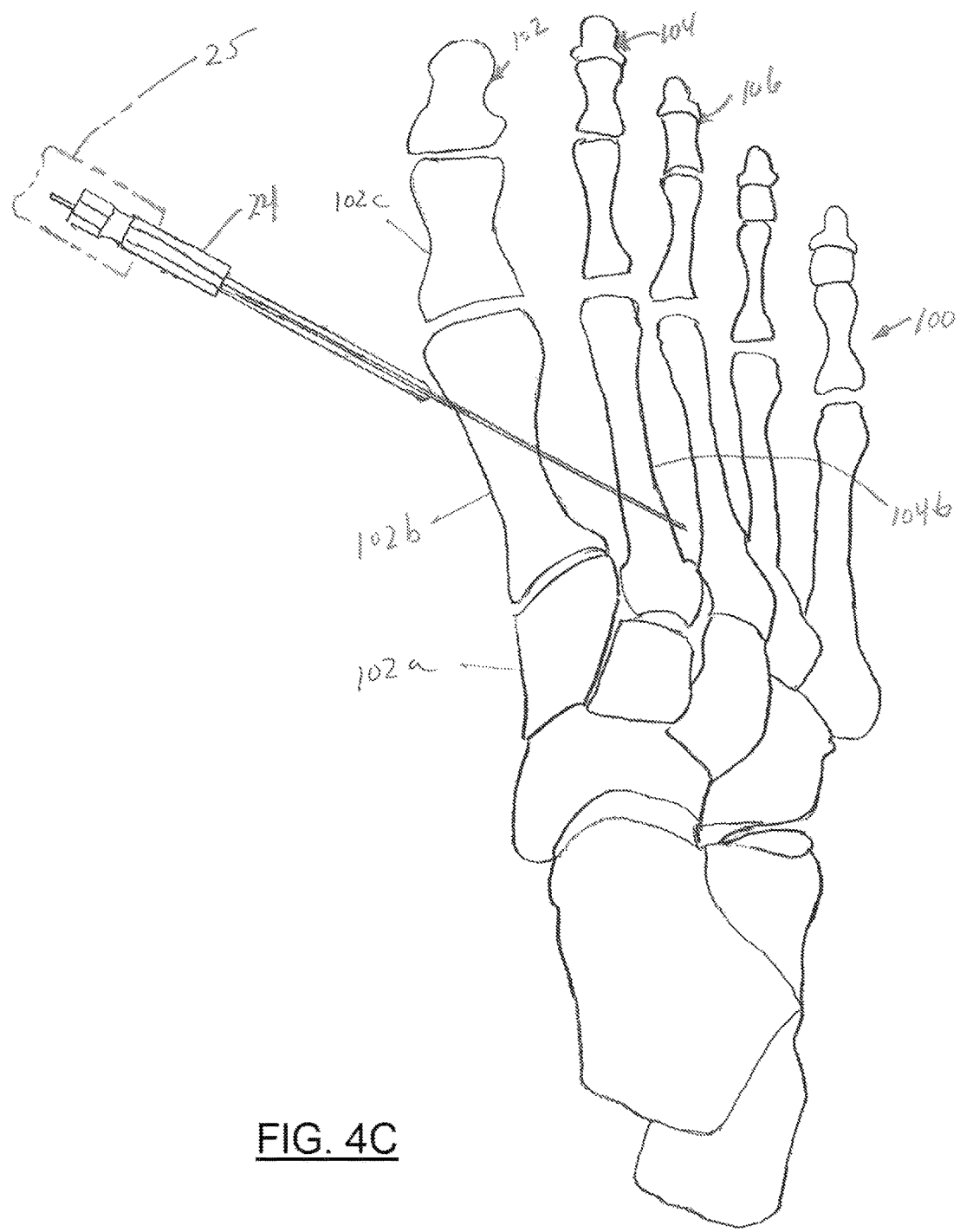
FIG. 4C is a schematic outline of the skeletal foot of FIG. 4A during a second step of bunion repair.

Then, as shown in FIG. 4C, in a second step, the drill bit 24, having the through bore 38 is placed coaxially over the K-wire, and with the K-wire acting as a guide, cuts a bore 110 (FIG. 4D) through the first and second metatarsals over the K-wire. The drill bit 24 is driven by a drill (not shown), having a drill chuck 25.

Figure 4D:
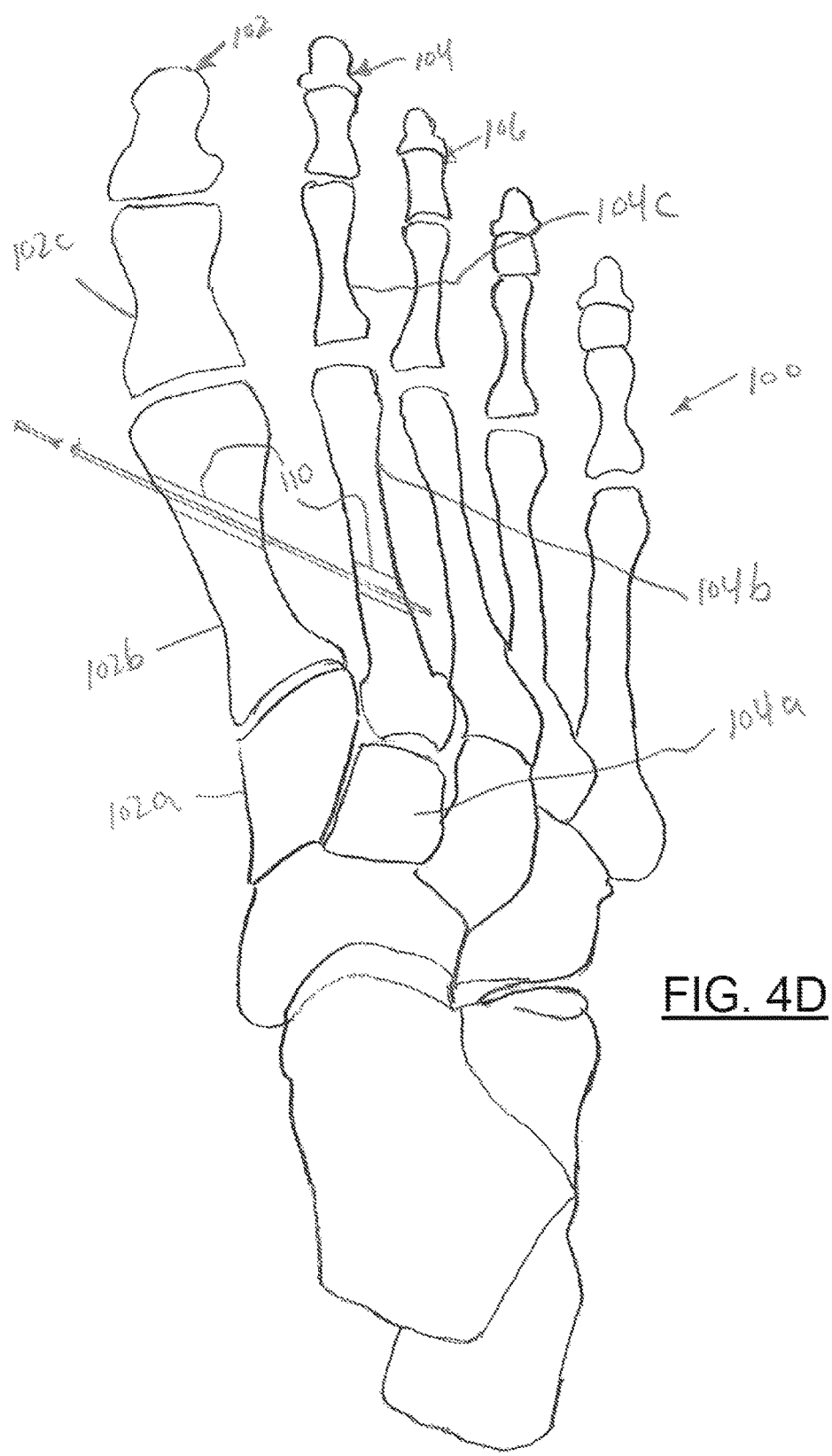
FIG. 4D is a schematic outline of a skeletal foot of FIG. 4A during a third step of bunion repair.

FIG. 4D illustrates the K-wire 103 remaining in the bore 110 through the first and second metatarsal bones, once the drill bit 24 has been retracted in a third step.

Figure 4E:
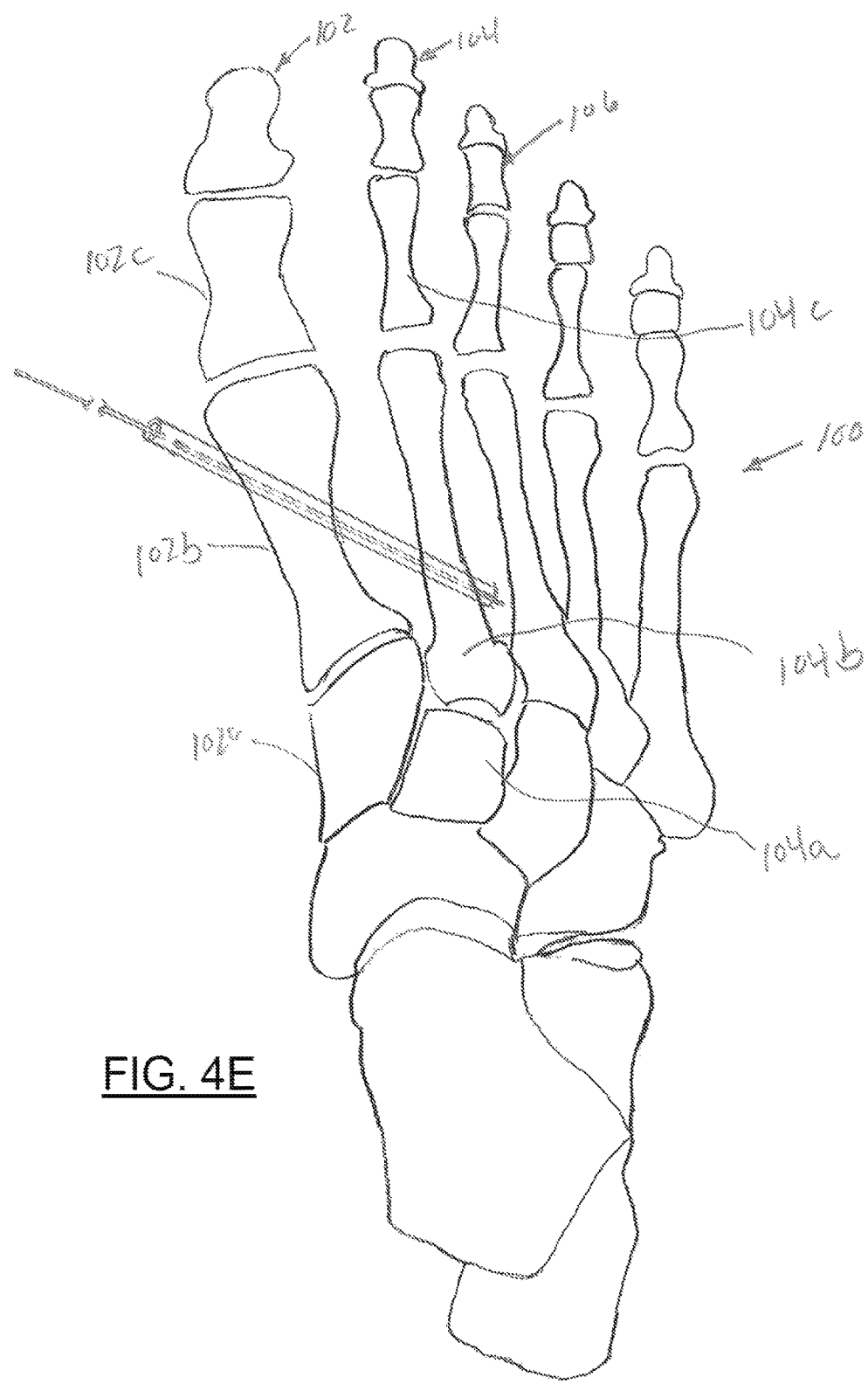
FIG. 4E s a schematic outline of a skeletal foot of FIG. 4A during a fourth step of bunion repair.

As shown in FIG. 4E, a tube 32, in a fourth step, has been inserted over the K-wire 103 and through the bore 110. The tube 32 fits tightly within the first and second metatarsal 102b, 104b and spans therebetween.

Figure 4F:
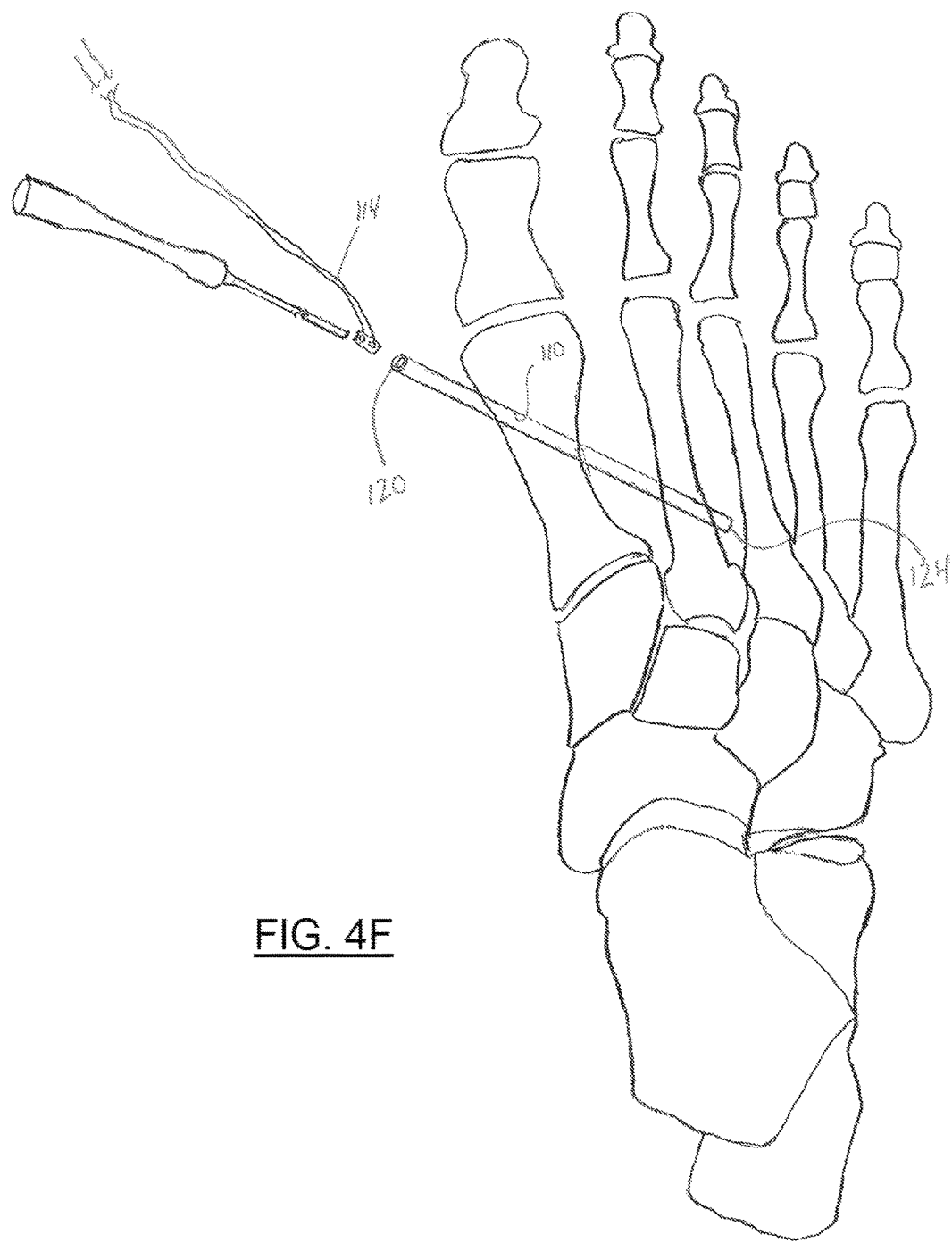
FIG. 4F is a schematic outline of a skeletal foot of FIG. 4A during fifth, sixth and seventh steps of bunion repair.

FIG. 4F illustrates the K-wire 103 has been removed in a fifth step, and first plate 28 has sutures or FIBER WIRE 114 threaded through the holes 28a, 28b. In a sixth step, the plate 28 with trailing FIBER WIRE 114 is entered into an open end 120 of the tube 32. The pusher 26 is used to push the plate 28 through the tube 32 from the open end 120 and out of the opposite open end 124. Once the plate 28 emerges from the opposite open end 124, the tube is withdrawn in a seventh step.

Figure 4G:
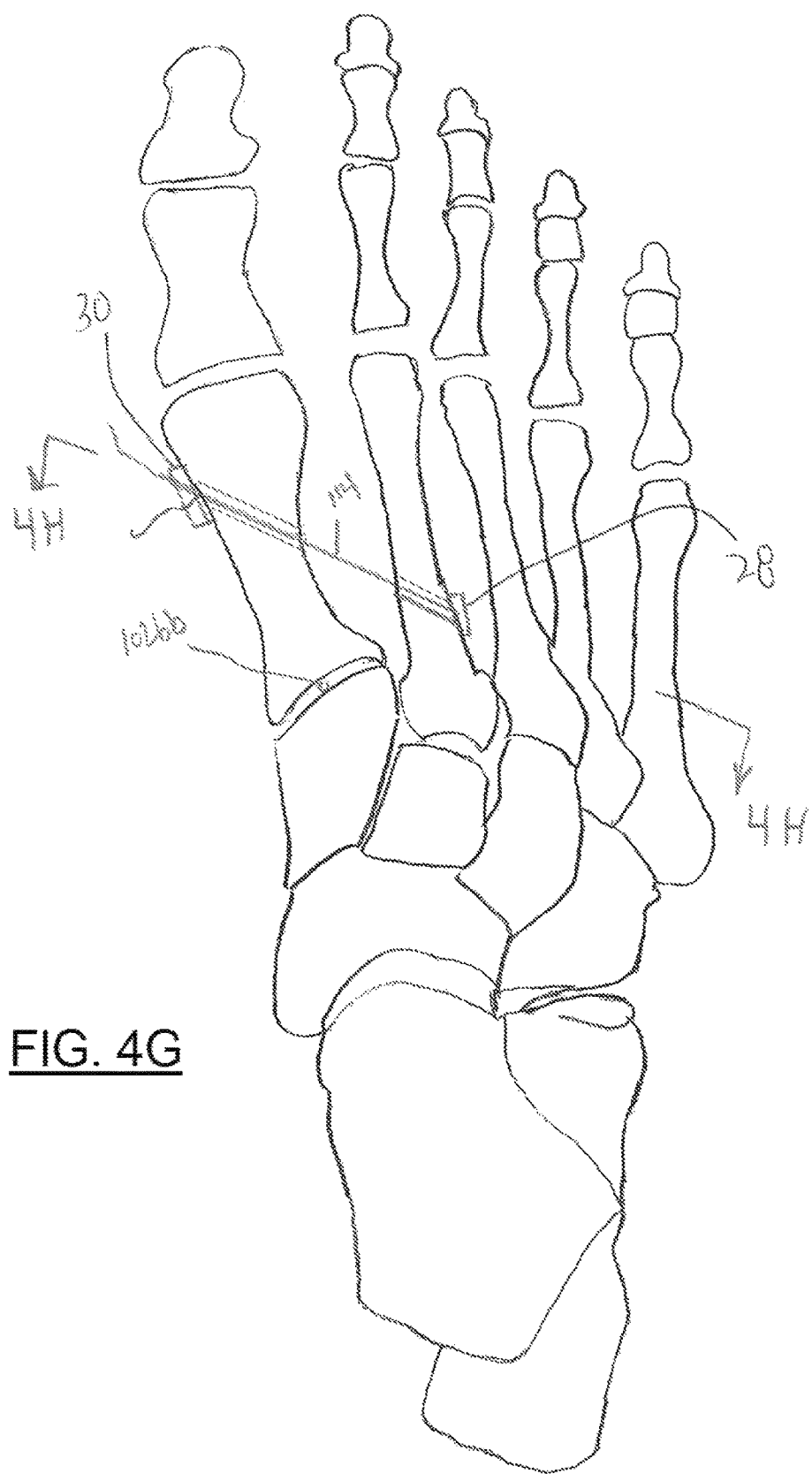
FIG. 4G is a schematic outline of a skeletal foot of FIG. 4A showing an eighth and ninth steps of bunion repair.
Figure 4H:
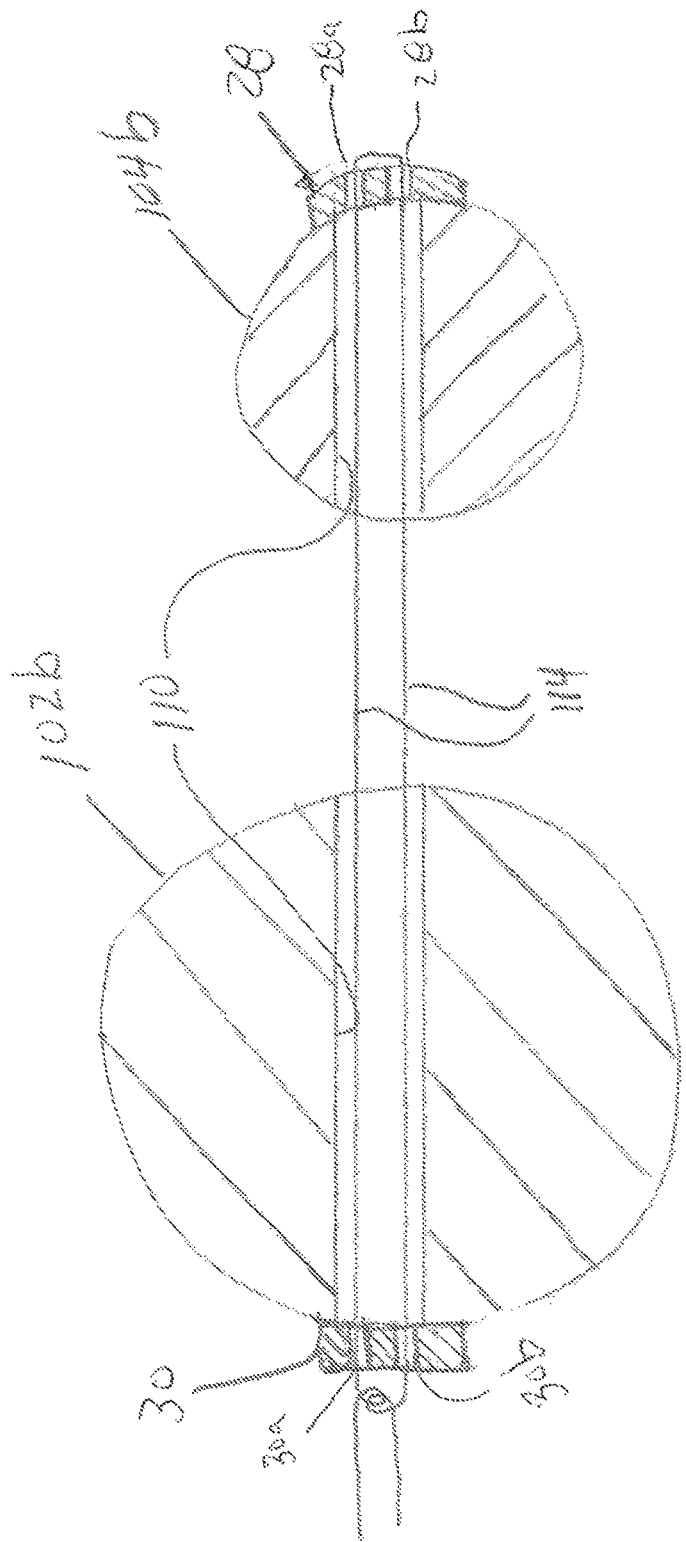
FIG. 4H is a sectional view taken generally along line 4H-4H of FIG. 4G.

As shown in FIGS. 4G and 4H, as the tube is withdrawn, or after the tube is withdrawn, in an eighth step, the plate 28 is rotated approximately 90° so that the plate 28 will brace against the second metatarsal 104b and cannot be pulled back through the bore 110 as the tube is withdrawn. Also, once the tube 32 is withdrawn, in a ninth step, the second plate 30 is placed against an outside of the first metatarsal 102b as sutures are drawn tight to the second plate 30. The sutures 114, under tension, hold the first metatarsal 102b in position with respect to the second metatarsal 104b to prevent the first metatarsal from rotating counterclockwise about the interface 102bb.

Although the plates 28, 30 are described to be installed adjacent to the second metatarsal 104b and the first metatarsal 102b respectively, depending on conditions, the plate 28 could be used against the first metatarsal 102b with the plate 30 used against the second metatarsal 104b, or two plates 30, 30 could be used against the two metatarsals 102b, 104b or two plates 28, 28 could be used against the two metatarsals 102b, 104b.

FIG. 4H shows the plates 28, 30 against the metatarsals but also indicates that the k-wire, the bore and the tube are all placed though a center line of the thickness of the metatarsals 102b, 104b.

From the foregoing, it will be observed that numerous variations and modifications may be effected without departing from the spirit and scope of the invention. It is to be understood that no limitation with respect to the specific apparatus illustrated herein is intended or should be inferred.

The invention claimed is:

1. A bunion repair tool assembly, comprising:
   a drill bit having an axial through bore for guiding the drill bit over a wire to drill through first and second metatarsals, forming a drilled bore;
   a tube sized to be inserted into the drilled bore spanning between the first and second metatarsals;
   a first plate connected to a length of suture or FIBER WIRE, the first plate having a profile to fit through the tube in one orientation and to be larger than the drilled bore in another orientation at the second metatarsal;
   a pusher sized to push the first plate from a base end of the tube, through the tube to exit out of the distal end of the tube; and
   a second plate for being connected to the length of suture or FIBER WIRE and being sized to be larger than the drilled bore at the first metatarsal.

2. The assembly according to claim 1, wherein the drill bit has a drill portion and a base portion, the drill portion has a diameter of about 4 mm, and a drill length of about 80 mm and the axial through bore has a diameter of about 1.2 mm and extends from an open tip end to an open base end.

3. The assembly according to claim 1, wherein the pusher includes a handle, a pushing shank with a diameter of about 1.3 mm and a length of about 100 mm.

4. The assembly according to claim 1, wherein the first plate includes two holes for receiving a suture or FIBER WIRE, and a curved face which allows the plate to fit comfortably against the second metatarsal.

5. The assembly according to claim 1 wherein the second plate includes two holes for receiving a suture or FIBER WIRE.

6. The assembly according to claim 1 wherein the tube has a length of about 90 mm and a diameter of about 3.9 mm.

7. The assembly according to claim 1, wherein the first plate is oblong-shaped having at least two apertures.

* * * * *